United States Patent
Stürmer

(10) Patent No.: US 7,435,563 B2
(45) Date of Patent: Oct. 14, 2008

(54) METHOD FOR THE PRODUCTION OF (S)-3-METHYLAMINO-1-(THIEN-2-YL) PROPAN-1-OL

(75) Inventor: Rainer Stürmer, Rödersheim-Gronau (DE)

(73) Assignee: BASF Aktiengesellschaft (DE)

( * ) Notice: Subject to any disclaimer, the term of this patent is extended or adjusted under 35 U.S.C. 154(b) by 449 days.

(21) Appl. No.: 10/522,888

(22) PCT Filed: Jul. 31, 2003

(86) PCT No.: PCT/EP03/08492

§ 371 (c)(1),
(2), (4) Date: Jun. 24, 2005

(87) PCT Pub. No.: WO2004/013123

PCT Pub. Date: Feb. 12, 2004

(65) Prior Publication Data
US 2005/0245749 A1    Nov. 3, 2005

(30) Foreign Application Priority Data
Aug. 1, 2002   (DE) ................. 102 35 206

(51) Int. Cl.
*C07D 333/16* (2006.01)
*C07D 333/22* (2006.01)
(52) U.S. Cl. ............... 435/91.53; 549/75; 549/76
(58) Field of Classification Search ............ 435/91.53; 549/75, 76
See application file for complete search history.

(56) References Cited

U.S. PATENT DOCUMENTS 5,254,737 A * 10/1993 Zimmerman ............. 564/490

5,491,243 A   2/1996 Berglund

FOREIGN PATENT DOCUMENTS

| EP | 0 273 658 | 7/1988 |
| EP | 0 457 559 | 11/1991 |
| EP | 0 650 965 | 10/1994 |

OTHER PUBLICATIONS

Kamal et al. "Chemoenzymatic synthesis of duloxetine and its enantiomer: lipase-catalyzed resolution of 3-hydroxy-3-(2-thienyl) propanenitrile" Tetrahedron Letters, 2003, vol. 44, pp. 4783-4787.*
Deeter et al. "Asymmetric Synthesis and Absolute Stereochemistry of LY248686" Tetrahedron Letters, 1990, vol. 31, pp. 7101-7104.*
Pamies, O., Bäckvall, J.E. in Advanced Synthesis and Catalysis, vol. 343, No. 6-7, 2001, pp. 726-731.
Deeter, J. et al. in Tetrahedron Letters, vol. 31, No. 49, pp. 7101-7104, 1990.

* cited by examiner

*Primary Examiner*—Rei-tsang Shiao
*Assistant Examiner*—Joseph R Kosack
(74) *Attorney, Agent, or Firm*—Connolly Bove Lodge & Hutz LLP

(57) ABSTRACT

The present invention relates to a process for the preparation of enantiomerically pure (S)-3-methyl-amino-1-(thien-2-yl) propan-1-ol of the formula II-S

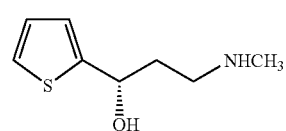

by obtainment of (S)-3-hydroxy-3-thien-2-ylpropionitrile from its enantiomer mixture with the R isomer and the subsequent reaction of (S)-3-hydroxy-3-thien-2-ylpropionitrile with hydrogen and methylamine in the presence of a catalyst to give II-S.

9 Claims, No Drawings

METHOD FOR THE PRODUCTION OF (S)-3-METHYLAMINO-1-(THIEN-2-YL) PROPAN-1-OL

RELATED APPLICATIONS

This application is a national stage application (under 35 U.S.C. 371) of PCT/EP2003/08492 filed Jul. 31, 2003, which claims benefit of German application 102 35 206.2 filed Aug. 1, 2002.

The present invention relates to a process for the preparation of enantiomerically pure (S)-3-methyl-amino-1-(thien-2-yl)propan-1-ol of the formula II-S

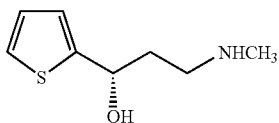

The aminopropanol II-S is an important precursor for the synthesis of the antidepressant duloxetine of the formula IV

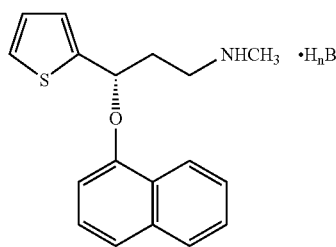

in which B is an n times negatively charged inorganic or organic acid radical and $H_nB$ is a pharmaceutically tolerable acid.

Duloxetine is accordingly the acid addition salt of the aminonaphthyl ether III (subsequently described as duloxetine base III)

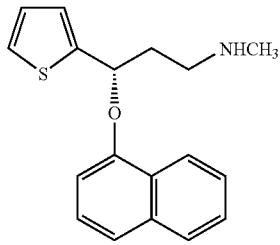

Processes of the prior art for the preparation of duloxetine base III are laborious and necessitate the use of chiral reagents or chiral starting materials.

Thus EP-B-0273658 describes a process for the preparation of duloxetine base III by reaction of 2-acetylthiophene in a Mannich reaction with formaldehyde and dimethylamine, reduction of the keto group of the Mannich base V obtained in this reaction to the racemic (S)-3-N,N-dimethylamino-1-(thien-2-yl)propan-1-ol VI, etherification of the alcohol function with naphthyl fluoride and finally conversion of the dimethylamino group into a methylamino function. The desired enantiomer of the naphthyl ether III is obtained by use of chiral starting materials or by resolution of racemates at the stage of the final product, for example via the salts using optically active acids or chromatography on a chiral stationary phase.

U.S. Pat. No. 5,362,886 describes an analogous process, in which the racemic alcohol VI obtained after reduction of the keto group is treated with S-mandelic acid. The S enantiomer of VI obtained in this process is employed in the subsequent reaction stages.

EP-A-0457559 likewise describes a process analogous to EP-B-0273658. In this process, the keto group of the Mannich base V is reduced to the S enantiomer of VI using the asymmetric reduction system LAH-lcb (lithium aluminum hydride-[(2R,2S)-(−)-4-dimethylamino-1,2-di-phenyl-3-methyl-2-butanol]). In addition to the costs, the sensitivity of the reduction system LAH-lcb, which is only stable for a few minutes, is disadvantageous here.

The object of the present invention was the provision of an economical process for the preparation of the aminoalcohol II-S.

It has surprisingly been found that the alcohol II-S can be prepared enantioselectively from enantiomer mixtures of the alcohols I-S and I-R, in particular from racemic alcohol I, by first acylating the enantiomer mixture in the presence of a hydrolase and separating the acylation product of the alcohol I-R formed here from the unreacted alcohol I-S. The alcohol I-S can then be converted selectively into the alcohol II-S in high yields by reduction of the nitrile group in the presence of methylamine without racemization taking place.

The invention thus relates to a process for the preparation of enantiomerically pure (S)-3-methylamino-1-(thien-2-yl) propan-1-ol of the formula II-S

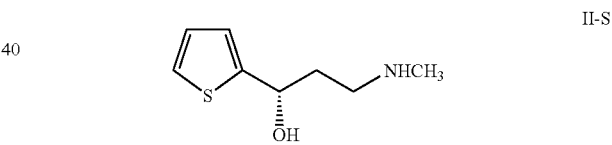

comprising the following steps:
a) reaction of an enantiomer mixture of the alcohols (S)-3-hydroxy-3-thien-2-ylpropionitrile and (R)-3-hydroxy-3-thien-2-ylpropionitrile of the formulae I-S and I-R

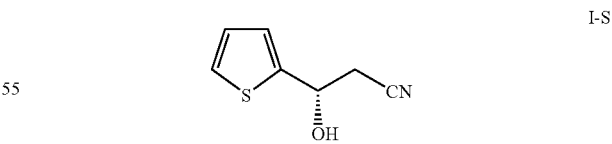

with an acylating agent in the presence of a hydrolase, a mixture of essentially unacylated alcohol I-S and essentially acylated alcohol I-R being obtained;

b) separation of the alcohol I-S from the mixture obtained in step a); and c) reaction of the alcohol I-S with hydrogen and methylamine in the presence of a catalyst to give (S)-3-methylamino-1-(thien-2-yl)propan-1-ol II-S.

"Essentially unacylated alcohol I-S" should be understood as meaning that at least 95%, preferably at least 98%, in particular at least 99%, of the alcohol I-S is unacylated. Analogously, it holds for the expression "essentially acylated alcohol I-R" that at least 95%, preferably at least 97%, particularly preferably at least 98%, of the alcohol I-R is present in acylated form.

The hydrolase employed in step a) is a lipase or an esterase. This brings about selective esterification of the alcohol I-R. The hydrolase is preferably obtained from a microorganism, particularly preferably from a bacterium or fungus. Particularly preferably, it is of bacterial origin. Likewise suitable are hydrolases which are obtainable by recombinant processes. The hydrolase can be used in purified or partially purified form or in the form of the microorganism itself. Processes for the obtainment and purification of hydrolases from microorganisms are adequately known to the person skilled in the art, e.g. from EP 1 149 849 or EP-A 1 069 183.

The hydrolase can be employed in free or immobilized form. An immobilized enzyme is understood as meaning an enzyme which is fixed to an inert support. Suitable support materials and the enzymes immobilized thereon are known from EP-A 1149849, EP-A-1 069 183 and DE-A 100 19 377 and from the references cited therein. Reference is fully made regarding this to the disclosure of these specifications. The suitable support materials include clays, clay minerals, such as kaolinite, diatomaceous earths, perlite, silica, alumina, sodium carbonate, calcium carbonate, cellulose powder, anion exchange materials, synthetic polymers, such as polystyrene, acrylic resins, phenol-formaldehyde resins, polyurethanes and polyolefins, such as polyethylene and polypropylene. The support materials are customarily employed in a finely divided, particulate form for the preparation of the supported enzymes, porous forms being preferred. The particle size of the support material is customarily not more than 5 mm, in particular not more than the 2 mm (grading curve). Preferred support materials are microporous polymer particles having a cavity content of preferably 40 to 80% by vol. and pore sizes of preferably 10 nm to 1 µm, e.g. particulate polypropylene, which is marketed by the company Akzo under the name Accurel®.

Preferably, lipases (triacylglycerolacylhydrolases; EC 3.1.1.3) are employed. Preferred among these are lipases which are obtained from bacteria of the genera *Burkholderia* or *Pseudomonas*. Examples of *Burkholderia* species are *Burkholderia ambifaria* (e.g. strains ATCC BAA-244, CCUG 44356, LMG 19182); *Burkholderia andropogonis*, (e.g. strains ATCC 23061, CCUG 32772, CFBP 2421, CIP 105771, DSM 9511, ICMP 2807, JCM 10487, LMG 2129, NCPPB 934, NRRL B-14296); *Burkholderia caledonica* (e.g. strains W50D, CCUG 42236, CIP 107098, LMG 19076); *Burkholderia caribensis* (e.g. strains MWAP64, CCUG 42847, CIP 106784, DSM 13236, LMG 18531); *Burkhoderia caryophylli* (e.g. strains ATCC 25418, CCUG 20834, CFBP 2429, CFBP 3818, CIP 105770, DSM 50341, HAMBI 2159, ICMP 512, JCM 9310, JCM 10488, LMG 2155, NCPPB 2151); *Burkholderia cepacia* (e.g. strains Ballard 717, 717-ICPB 25, ATCC 25416, CCUG 12691, CCUG 13226, CFBP 2227, CIP 80.24, DSM 7288, HAMBI 1976, ICMP 5796, IFO 14074, JCM 5964, LMG 1222, NCCB 76047, NCPPB 2993, NCTC 10743, NRRL B-14810); *Burkholderia cocovenenans* (e.g. strains ATCC 33664, CFBP 4790, DSM 11318, JCM 10561, LMG 11626, NCIMB 9450); *Burkholderia fungorum* (e.g. strains Croize P763-2, CCUG 31961, CIP 107096, LMG 16225); *Burkholderia gladioli* (e.g. strains ATCC 10248, CCUG 1782, CFBP 2427, CIP 105410, DSM 4285, HAMBI 2157, ICMP 3950, IFO 13700, JCM 9311, LMG 2216, NCB 38018, NCPPB 1891, NCTC 12378, NRRL B-793); *Burkholderia glathei* (e.g. strains ATCC 29195, CFBP 4791, CIP 105421, DSM 50014, JCM 10563, LMG 14190); *Burkholderia glumae* (e.g. strains ATCC 33617, CCUG 20835, CFBP 4900, CFBP 2430, CIP 106418, DSM 9512, ICMP 3655, LMG 2196, NCPPB 2981, NIAES 1169); *Burkholderia graminis* (e.g. strains C4D1M, ATCC 700544, CCUG 42231, CIP 106649, LMG 18924); *Burkholderia kururiensis* (e.g. strains KP 23, ATCC 700977, CIP 106643, DSM 13646, JCM 10599, LMG 19447); *Burkholderia mallei* (e.g. strains ATCC 23344, NCTC 12938); *Burkholderia multivorans* (e.g. strains ATCC BAA-247, CCUG 34080, CIP 105495, DSM 13243, LMG 13010, NCTC 13007); *Burkholderia norimbergensis* (e.g. strains R2, ATCC BAA-65, CCUG 39188, CFBP 4792, DSM 11628, CIP 105463, JCM 10565, LMG 18379); *Burkholderia phenazinium* (e.g. strains ATCC 33666, CCUG 20836, CFBP 4793, CIP 106502, DSM 10684, JCM 10564, LMG 2247, NCIB 11027); *Burkholderia pickettii* (e.g. strains ATCC 27511, CCUG 3318, CFBP 2459, CIP 73.23, DSM 6297, HAMBI 2158, JCM 5969, LMG 5942, NCTC 11149); *Burkholderia plantarii* (e.g. strains AZ 8201, ATCC 43733, CCUG 23368, CFBP 3573, CFBP 3997, CIP 105769, DSM 9509, ICMP 9424, JCM 5492, LMG 9035, NCPPB 3590, NIAES 1723); *Burkholderia pseudomallei* (e.g. strains WRAIR 286, ATCC 23343, NCTC 12939); *Burkholderia pyrrocinia* (e.g. strains ATCC 15958, CFBP 4794, CIP 105874, DSM 10685, LMG 14191); *Burkholderia sacchari* (e.g. strains CCT 6771, CIP 107211, IPT 101, LMG 19450); *Burkholderia solanacearum* (e.g. strains A. Kelman 60-1, ATCC 11696, CCUG 14272, CFBP 2047, CIP 104762, DSM 9544, ICMP 5712, JCM 10489, LMG 2299, NCAIM B.01459, NCPPB 325, NRRL B-3212); *Burkholderia stabilis* (e.g. strains ATCC BAA-67, CCUG 34168, CIP 106845, LMG 14294, NCTC 13011); *Burkholderia thailandensis* (e.g. strains E 264, ATCC 700388, CIP 106301, DSM 13276); *Burkholderia ubonensis* (e.g. strains EY 3383, CIP 107078, NCTC 13147); *Burkholderia vandii* (e.g. strains VA-1316, ATCC 51545, CFBP 4795, DSM 9510, JCM 7957, LMG 16020); *Burkholderia vietnamiensis* (e.g. strains TVV 75, ATCC BAA-248, CCUG 34169, CFBP 4796, CIP 105875, DSM 11319, JCM 10562, LMG 10929). Examples of *Pseudomonas* species are *Pseudomonas aeruginosa* (e.g. strains ATCC 10145, DSM 50071), *Pseudomonas agarici* (e.g. strains ATCC 25941, DSM 11810), *Pseudomonas alcaligenes* (e.g. strains ATCC 14909, DSM 50342), *Pseudomonas amygdali* (e.g. strains ATCC 337614, DSM 7298), *Pseudomonas anguiliseptica* (e.g. strains ATCC 33660, DSM 12111), *Pseudomonas antimicrobica* (e.g. strains DSM 8361, NCIB 9898, LMG 18920), *Pseudomonas aspleni* (e.g. strains ATCC 23835, CCUG 32773), *Pseudomonas aurantiaca* (e.g. strains ATCC 33663, CIP 106710), *Pseudomonas aureofaciens* (e.g. strains ATCC 13985, CFBP 2133), *Pseudomonas avellanae* (e.g. strains DSM 11809, NCPPB 3487), *Pseudomonas azotoformans* (e.g. strains CIP 106744, JCM 7733), *Pseudomonas balearica* (e.g. strains DSM 6083, CIP 105297), *Pseudomonas beijerinsckii* (e.g. strains ATCC 19372, DSM 6083), *Pseudomonas beteli* (e.g. strains ATCC 19861, CFBP 4337), *Pseudomonas boreopolis* (e.g. strains ATCC 33662, CIP 106717), *Pseudomonas carboxyhydrogena* (e.g. strains ATCC 29978, DSM 1083), *Pseudomonas caricapapayae* (e.g. strains ATCC 33615, CCUG 32775), *Pseudomonas* cichorii (e.g. strains ATCC 10857, DSM 50259), *Pseudomonas cissicola* (e.g. strains ATCC 33616, CCUG 18839), *Pseudomonas citronellolis* (e.g. strains ATCC 13674, DSM 50332), *Pseudomonas coronafaciens* (e.g. strains DSM 50261, DSM 50262), *Pseudomonas corrugata* (e.g. strains ATCC 29736, DSM 7228), *Pseudomonas doudoroffii* (e.g. strains ATCC 27123, DSM 7028), *Pseudomonas echinoides* (e.g. strains ATCC 14820, DSM 1805), *Pseudomonas elongata* (e.g. strains ATCC 10144, DSM 6810), *Pseudomonas ficuserectae* (e.g. strains ATCC 35104, CCUG 32779), *Pseudomonas flavescens* (e.g. strains ATCC 51555, DSM 12071), *Pseudomonas flectens* (e.g. strains ATCC 12775, CFBB 3281), *Pseudomonas fluorescens* (e.g. strains ATCC 13525, DSM 50090), *Pseudomonas fragi* (e.g. strains ATCC 4973, DSM 3456), *Pseudomonas fulva* (e.g. strains ATCC 31418, CIP 106765), *Pseudomonas fuscovaginae* (e.g. strains CCUG 32780, DSM 7231), *Pseudomonas gelidicola* (e.g. strains CIP 106748), *Pseudomonas geniculata* (e.g. strains ATCC 19374, LMG 2195), *Pseudomonas glathei* (e.g. strains ATCC 29195, DSM 50014), *Pseudomonas halophila* (e.g. strains ATCC 49241, DSM 3050), *Pseudomonas hibiscicola* (e.g. strains ATCC 19867, LMG 980), *Pseudomonas huttiensis* (e.g. strains ATCC 14670, DSM 10281), *Pseudomonas iners* (e.g. Stamm CIP 106746), *Pseudomonas lancelota* (e.g. strains ATCC 14669, CFBP 5587), *Pseudomonas lemoignei* (e.g. strains ATCC 17989, DSM 7445), *Pseudomonas lundensis* (e.g. strains ATCC 19968, DSM 6252), *Pseudomonas luteola* (e.g. strains ATCC 43273, DSM 6975), *Pseudomonas marginalis* (e.g. strains ATCC 10844, DSM 13124), *Pseudomonas meliae* (e.g. strains ATCC 33050, DSM 6759), *Pseudomonas mendocina* (e.g. strains ATCC 25411, DSM 50017), *Pseudomonas mucidolens* (e.g. strains ATCC 4685, CCUG 1424), *Pseudomonas monteilli* (e.g. strains ATCC 700476, DSM 14164), *Pseudomonas nautica* (e.g. strains ATCC 27132, DSM 50418), *Pseudomonas nitroreducens* (e.g. strains ATCC 33634, DSM 14399), *Pseudomonas oleovorans* (e.g. strains ATCC 8062, DSM 1045), *Pseudomonas oryzihabitans* (e.g. strains ATCC 43272, DSM 6835), *Pseudomonas pertucinogena* (e.g. strains ATCC 190, CCUG 7832), *Pseudomonas phenazinium* (e.g. strains ATCC 33666, DSM 10684), *Pseudomonas pictorum* (e.g. strains ATCC 23328, LMG 981), *Pseudomonas pseudoalcaligenes* (e.g. strains ATCC 17440, DSM 50188), *Pseudomonas putida* (e.g. strains ATCC 12633, DSM 291), *Pseudomonas pyrrocinia* (e.g. strains ATCC 15958, DSM 10685), *Pseudomonas resinovorans* (e.g. strains ATCC 14235, CCUG 2473), *Pseudomonas rhodesiae* (e.g. strains CCUG 38732, DSM 14020), *Pseudomonas saccharophila* (e.g. strains ATCC 15946, DSM 654), *Pseudomonas savastanoi* (e.g. strains ATCC 13522, CFBP 1670), *Pseudomonas spinosa* (e.g. strains ATCC 14606), *Pseudomonas stanieri* (e.g. strains ATCC 27130, DSM 7027), *Pseudomonas straminae* (e.g. strains ATCC 33636, CIP 106745), *Pseudomonas stutzeri* (e.g. strains ATCC 17588, DSM 5190), *Pseudomonas synxantha* (e.g. strains ATCC 9890, CFBP 5591), *Pseudomonas syringae* (e.g. strains ATCC 19310, DSM 6693), *Pseudomonas syzygii* (e.g. strains ATCC 49543, DSM 7385), *Pseudomonas taetrolens* (e.g. strains ATCC 4683, CFBP 5592), *Pseudomonas tolaasii* (e.g. strains ATCC 33618, CCUG 32782), *Pseudomonas veronii* (e.g. strains ATCC 700272, DSM 11331), *Pseudomonas viridiflava* (e.g. strains ATCC 13223, DSM 11124), *Pseudomonas vulgaris, Pseudomonas wisconsinensis* and *Pseudomonas* spec. DSM 8246. Of these, lipases from *Burkholderia glumae, Burkholderia plantarii, Burkholderia cepacia, Pseudomonas aeruginosa, Pseudomonas fluorescens, Pseudomonas fragi, Pseudomonas luteola, Pseudomonas vulgaris, Pseudomonas wisconsinensis* and *Pseudomonas* spec. DSM 8246 are preferred. Lipases from *Pseudomonas* spec. DSM 8246 are particularly preferred. In preferred embodiments, the lipases employed are enzyme preparations which are obtainable from *Pseudomonas* spec. DSM 8246 or *Burkolderia plantarii* by fermentation of the bacterium and drying of the supernatant; supported lipases from *Burkolderia cepacia*, which are immobilized on ceramic or diatomite and are marketed by Amano Pharmaceutical Co., Tokyo, Japan under the name Amano PS-C I, Amano PS-C II or Amano PS-D; and enzyme preparations from *Burkholderia glumae*. The fermentation of the bacteria is carried out, for example, as described in EP-A 1 069 183, to which reference is hereby fully made.

The acylating agents used in step a) are, for example, vinyl, propenyl or isopropenyl esters of aliphatic monocarboxylic acids having 2 to 20 carbon atoms, preferably having 3 to 12 carbon atoms and particularly preferably having 3 to 8 carbon atoms. Likewise suitable are the vinyl, propenyl and isopropenyl esters of aliphatic dicarboxylic acids having 2 to 20 carbon atoms, preferably of dicarboxylic acids having 3 to 12 carbon atoms and particularly preferably having 4 to 8 carbon atoms. Suitable acylating agents are also acid anhydrides of aliphatic monocarboxylic acids having 2 to 12 carbon atoms, preferably having 3 to 8 carbon atoms, and acid anhydrides of aliphatic dicarboxylic acids having 4 to 12 carbon atoms, preferably having 4 or 5 carbon atoms.

Examples of the vinyl, propenyl or isopropenyl esters of aliphatic monocarboxylic acids having 2 to 20 carbon atoms are the vinyl, propenyl or isopropenyl esters of acetic acid, propionic acid, butyric acid, isobutyric acid, valeric acid, isovaleric acid, 2-methylbutyric acid, caproic acid, 2-methylvaleric acid, 3-methylvaleric acid, 4-methylvaleric acid, 2,2-dimethylbutyric acid, 3,3-dimethylbutyric acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid and arachic acid. Among the aforementioned esters, the vinyl esters are preferred.

Examples of the vinyl, propenyl or isopropenyl esters of aliphatic dicarboxylic acids having 2 to 20 carbon atoms are the vinyl, propenyl or isopropenyl esters of oxalic acid, malonic acid, succinic acid, methyl-, dimethyl-, trimethyl- and tetramethylsuccinic acid, glutaric acid, 3,3-dimethylglutaric acid, adipic acid, pimelic acid, azelaic acid, sebacic acid, maleic acid, fumaric acid and sorbic acid. Among the aforementioned esters, the vinyl esters are preferred.

Examples of the acid anhydrides of aliphatic monocarboxylic acids having 2 to 12 carbon atoms are the acid anhydrides of the abovementioned carboxylic acids, e.g. those of propionic acid, butyric acid, isobutyric acid, valeric acid, isovaleric acid, 2-methylbutyric acid, caproic acid, 2-methylvaleric acid, 3-methylvaleric acid, 4-methylvaleric acid, 2,2-dimethylbutyric acid, 3,3-dimethylbutyric acid, enanthic acid and caprylic acid. Among the aforementioned anhydrides, those of propionic acid, butyric acid, valeric acid and caproic acid are preferred.

Examples of the acid anhydrides of aliphatic dicarboxylic acids having 4 to 12 carbon atoms are succinic anhydride, methylsuccinic anhydride, dimethylsuccinic anhydride, trimethylsuccinic anhydride, tetramethylsuccinic anhydride, glutaric anhydride and 3,3-dimethylglutaric anhydride. Among these, succinic anhydride and glutaric anhydride are preferred.

Among the acylating agents employed in step a), the vinyl esters of aliphatic $C_3$-$C_{12}$-monocarboxylic acids, in particular of $C_3$-$C_8$-monocarboxylic acids, such as propionic acid, butyric acid, valeric acid, caproic acid, enanthic acid and caprylic acid; the vinyl esters of a aliphatic $C_3$-$C_{12}$-dicarboxylic acids, in particular of $C_4$-$C_8$-dicarboxylic acids, such as succinic acid, adipic acid, pimelic acid, azelaic acid and sebacic acid; and the acid anhydrides of aliphatic $C_4$-$C_{12}$-dicarboxylic acids, in particular of dicarboxylic acids having 4 or 5 carbon atoms, such as succinic acid and adipic acid, are preferred. This applies in particular if the enzyme employed is a lipase, especially a lipase from a bacterium of the genus *Burkholderia* or *Pseudomonas*.

Preferably, in step a) 0.6 to 2 equivalents, particularly preferably 1 to 1.5 mol equivalents and in particular 1 to 1.2 mol equivalents of the acylating agent, based on the content of alcohol I-R in the mixture of enantiomers, are employed in the reaction. Mole equivalents are understood as meaning the number of carboxyl groups of the acylating agent in moles which can react with 1 mol of alcohol I-R. Correspondingly, in the use of the vinyl, propenyl or isopropenyl esters of aliphatic monocarboxylic acids and of acid anhydrides of aliphatic mono- or dicarboxylic acids, preferably 1.6 to 2 mol, particularly preferably 1 to 1.5 mol and in particular 1 to 1.2 mol of the acylating agent are employed, based on 1 mol of the alcohol I-R contained in the mixture of enantiomers, while in the use of vinyl, propenyl or isopropenyl esters of aliphatic dicarboxylic acids, preferably 0.3 to 1 mol, particularly preferably 0.5 to 0.8 mol and in particular 0.5 to 0.6 mol of acylating agent per mole of I-R, are employed.

In a preferred embodiment, the reaction in step a) is carried out in a nonaqueous reaction medium. Non-aqueous reaction media should be understood as meaning reaction media which contain less than 1% by weight, preferably less than 0.5% by weight, of water, based on the total weight of the reaction medium. Preferably, the reaction is carried out in an organic solvent. Suitable solvents are, for example, aliphatic hydrocarbons, preferably having 5 to 8 carbon atoms, such as pentane, cyclopentane, hexane, cyclohexane, heptane, octane or cyclooctane, halogenated aliphatic hydrocarbons, preferably having one or two carbon atoms, such as dichloromethane, chloroform, carbon tetrachloride, dichloroethane or tetrachloroethane, aromatic hydrocarbons, such as benzene, toluene, the xylenes, chlorobenzene or dichlorobenzene, aliphatic acyclic and cyclic ethers, preferably having 4 to 8 carbon atoms, such as diethyl ether, methyl tert-butyl ether, ethyl tert-butyl ether, dipropyl ether, diisopropyl ether, dibutyl ether, tetrahydrofuran or dioxane or mixtures thereof. The aforementioned ethers, in particular tetrahydrofuran, are particularly preferably used.

The reactants are preferably employed in a concentration of 1 g/l to 500 g/l, in particular of 100 g/l to 500 g/l.

In a further preferred embodiment of the process according to the invention, the reaction in step a) takes place in substance, i.e. without aqueous or organic solvent. In this case, the acylating agent is preferably selected from the abovementioned vinyl, propenyl or isopropenyl esters, in particular the vinyl esters.

The reaction in step a) is as a rule carried out at a reaction temperature below the deactivation temperature of the hydrolase employed and preferably at at least −10° C. Particularly preferably, it lies in the range from 0 to 100° C., in particular from 20 to 60° C. and especially from 2 to 40° C. Particularly preferably, the reaction is carried out at the temperature at which the hydrolase has its highest activity.

For carrying out the reaction, it is possible, for example, to introduce the mixture of the alcohols I-R and I-S with the hydrolase, the acylating agent and optionally the solvent and to thoroughly mix the mixture, e.g. by stirring or shaking.

However, it is also possible to immobilize the hydrolase in a reactor, for example in a column, and to lead a mixture containing the alcohol I and the acylating agent through the reactor. For this, the mixture can be led in circulation through the reactor until the desired conversion is achieved. In this process, the carboxyl groups of the acylating agent are sequentially converted into esters of the R enantiomer, while the S enantiomer remains essentially unchanged. As a rule, the esterification in step a) is carried out up to a conversion of at least 95%, particularly preferably of at least 99% and in particular of at least 99.5%, based on the alcohol I-R contained in the mixture. The progress of the reaction, i.e. the sequential esterification of the alcohol I-R, can be monitored here by customary methods such as gas chromatography.

The mixture of enantiomers of the alcohols I-R and I-S employed is preferably their racemate.

The reaction mixture can be worked up in the customary manner, for example by first separating the hydrolase from the reaction mixture, e.g. by filtering off or centrifuging off, optionally removing the solvent from the filtrate or centrifugate and then subjecting the residue to a separation operation. Suitable separation operations are, for example, extraction, distillation, crystallization or chromatography, the separation operation being selected depending on the acylating agent used. Thus a reaction mixture which is obtained in the reaction of I with vinyl, propenyl or isopropenyl esters of aliphatic dicarboxylic acids, is preferably separated by distillation, while a reaction mixture in which the vinyl, propenyl or isopropenyl esters of aliphatic monocarboxylic acids, acid anhydrides of aliphatic monocarboxylic acids or acid anhydrides of aliphatic dicarboxylic acids were employed as acylating agents in step a) are preferably separated by extraction.

However, it is also possible to subject the entire reaction mixture from step a), if appropriate with prior separation of the solvent, directly to the separation operation, where, however, the prior separation of the enzyme is preferred.

The enantiomeric excess of the alcohol I-S separated in step b) can be determined by means of customary processes, for example by determination of the optical rotation or by chromatography on a chiral phase, for example by HPLC or gas chromatography on chiral columns.

Using the process according to the invention, the alcohol I-S is obtained with an enantiomeric excess (ee value) of preferably at least 98%, particularly preferably of at least 99% and in particular of at least 99.4%.

The enantiomeric purity of the acylation product of I-R can be determined using the same processes. Preferably, the ee value is at least 97%, particularly preferably at least 98%.

A further preferred embodiment of the process according to the invention additionally comprises the steps:

b1) obtainment of an enantiomer mixture enriched in alcohol I-R from the residue obtained after separation of the alcohol I-S by hydrolysis of the residue, b2) racemization of this enantiomer mixture and b3 recovery of the racemate in step a).

The hydrolysis of the acylated alcohol I-R in step b1) can be carried out by customary processes, for example by reaction with a base. Suitable bases are, for example, alkali metal and alkaline earth metal hydroxides and carbonates, ammonia, amines, such as dimethylamine, diethylamine, trimethylamine, triethylamine and diisopropylamine. Preferably, sodium hydroxide or potassium hydroxide is used as a base for the hydrolysis. The hydrolysis can be carried out in water or in a solvent or in a mixture of water and solvent. Suitable solvents are alcohols, preferably having 1 to 3 carbon atoms, such as methanol, ethanol, propanol or isopropanol, glycols, in particular having 2 to 8 carbon atoms, such as ethylene glycol, di- and triethylene glycol, the mixtures of the abovementioned solvents and their mixtures with water.

The racemization of the enantiomer mixture obtained in step b1) from alcohol I-R not completely separated off in step b) and alcohol I-S obtained by hydrolysis of the acylation product can likewise be carried out by means of known processes, for example by reaction with an acid or preferably by oxidation of the alcohol function to a keto group and its reduction to the alcohol function. Suitable oxidants are known to the person skilled in the art. These include, for example, manganese dioxide, hydrogen peroxide, tungsten (VI) oxide.$H_2O_2$, activated DMSO systems (according to Corey or Swern), enzymatic systems (dehydrogenases) and others. Suitable reductants are likewise known to the person skilled in the art and include, for example, sodium borohydride and hydrogen (catalytic hydrogenation).

Suitable catalysts for the reaction in step c) are preferably selected from heterogeneous catalysts, which comprise at least one metal of the subgroup VIII, or from homogeneous catalysts, which comprise at least one metal of the subgroup VIII and at least one phosphorus-containing ligand.

Preferred heterogeneous catalysts comprise as metals of subgroup VIII platinum, palladium, nickel, ruthenium and/or rhodium, where the metals can be employed in elemental or oxidic form.

The metal can be applied to a support to increase the activity and/or stability. Suitable support materials include both metallic and nonmetallic materials, where these can be either porous or nonporous. Metallic supports preferably consist of high-alloy stainless steels. Porous nonmetallic supports preferably consist of activated carbons, silicates, alumina, argillaceous earths or zeolites. Nonporous metallic supports preferably consist of mineral materials, such as natural or synthetic minerals, glasses and ceramics, of plastics or of a combination of both. The metal content in the supported heterogeneous catalyst is as a rule 0.001 to 10% by weight, often 0.1 to 7% by weight, based on the weight of the support. Preferably, the support is selected from the abovementioned porous nonmetallic supports, in particular from activated carbon, silicates and alumina.

When using unsupported metals, these, in particular nickel, are preferably employed in the form of metal foams, as "Raney catalysts".

Preferred heterogeneous catalysts are elemental palladium and nickel, particularly preferably nickel and specifically Raney nickel.

The metals of subgroup VIII of the homogeneous catalysts are preferably selected from palladium, nickel, platinum, ruthenium and rhodium and particularly preferably from ruthenium and rhodium.

The phosphorus-containing ligands of the homogeneous catalysts are preferably $PF_3$, phospholes, phospha-benzoles and 1-, 2- and multidentate phosphine, phosphinite, phosphonite, phosphoramidite and phosphite ligands. The phosphorus atom is as a rule substituted by at least one alkyl, cycloalkyl, heterocycloalkyl, aryl, arylalkyl, heteroaryl or heteroarylalkyl group, which for its part can be substituted by one or more of these groups or by one of the phosphorus-containing ligands. Two or more groups can also together form a bridging unit.

The alkyl radicals on the phosphorus atom in particular contain 1 to 20 and especially 1 to 8 carbon atoms. They can be present branched or unbranched. Examples of these are methyl, ethyl, n-propyl, isopropyl, n-butyl, sec-butyl, isobutyl, tert-butyl, n-pentyl, 2- and 3-pentyl, 2- and 3-methylbutyl, neopentyl, n-hexyl, 2-, 3- and 4-hexyl, 2-, 3- and 4-methylpentyl, 2-ethyl-butyl, n-heptyl, n-octyl and 2-ethylhexyl.

The cycloalkyl group is preferably a $C_5$-$C_7$-cycloalkyl group such as cyclopentyl, cyclohexyl and cycloheptyl. The heterocycloalkyl group as a rule contains 2 to 6 carbon atoms and 1 to 3 heteroatoms, which are selected from oxygen, sulfur, monosubstituted nitrogen and disubstituted silicon. Examples of these are tetrahydrofuran, di- and tetrahydropyran, dioxane, pyrrolidine, piperidine, piperazine and morpholine.

Aryl is, for example, phenyl, tolyl, xylyl, mesityl, naphthyl, anthranyl, phenanthryl, naphthacenyl, preferably phenyl or naphthyl and in particular phenyl.

Heteroaryl is, for example, pyrrolyl, pyrazolyl, imidazolyl, indolyl, carbazolyl, pyridyl, quinolinyl, acridinyl, pyridazinyl, pyrimidinyl or pyrazinyl.

The above details and preferences accordingly hold for the arylalkyl and heteroarylalkyl substituents.

In multidentate phosphorus-containing ligands having at least two phosphorus atoms, these are preferably bridged via $C_1$-$C_5$ units, in particular via $C_2$-$C_4$ units, which can be saturated or unsaturated.

Preferred phosphorus-containing ligands are tris-(triphenylphosphine) and tris(tritolylphosphine).

Preferred homogeneous catalysts are rhodium tris-(triphenylphosphine) chloride ($RhCl(PPh_3)_3$; Wilkinson catalyst) and ruthenium bis(triphenylphosphine) dichloride ($RuCl_2(PPh_3)_2$).

In addition to the phosphorus-containing ligands, the metal complex optionally additionally contains ligands, e.g. halides, amines, carboxylates, sulfonates, hydride, CO, olefins, dienes, nitriles, nitrogen-containing heterocycles, aromatics and ethers.

The catalyst is preferably employed in an amount from 0.1 to 5 mol % of metal, based on the amount of the alcohol I-S employed.

The catalyst can also be employed as a precatalyst, i.e. the actual catalyst is first produced in situ by reacation of the precatalyst with a phophorus-containing ligand.

In the hydrogenation in step c), a heterogeneous catalyst is preferably used, particularly preferably a nickel or palladium catalyst, palladium preferably being employed supported on carbon, and in particular Raney nickel.

The reaction in step c) is preferably carried out in a suitable solvent.

Preferred solvents are $C_1$-$C_4$-alcohols, such as methanol, ethanol, propanol, isopropanol, butanol or tert-butanol, aliphatic acyclic or cyclic ethers, such as diethyl ether, dipropyl ether, methyl tert-butyl ether, tetrahydrofuran or dioxane, water or their mixtures. The methylamine employed in step c) can either be employed in gaseous form or as an aqueous solution, it preferably being used as an aqueous solution.

Preferably, it is employed in an amount of 1- 100 mol equivalents, particularly preferably of 10-20 mol equivalents, based on the amount of the alcohol I-S employed.

The reaction in step c) is preferably carried out at a pressure of 1 to 250 bar, particularly preferably of 10 to 200 bar, in particular of 50 to 150 bar. The reaction temperature is preferably 25 to 140° C., preferably 40 to 100° C.

The reaction can be worked up in a customary manner, for example by optionally first deactivating the catalyst and then separating it, removing the solvent and isolating clean II-S from the residue, for example by crystallization, distillation, extraction or chromatography.

By means of the process according to the invention, the methylaminopropanol II-S is obtained with an enantiomeric excess (ee value) of at least 98%, preferably of at least 99% and in particular of at least 99.4%.

The preparation of an enantiomer mixture of the alcohols I-S and I-R employed in step a) is carried out, for example, by reaction of thiophene-2-carbaldehyde with acetonitrile in the presence of a base according to the following scheme:

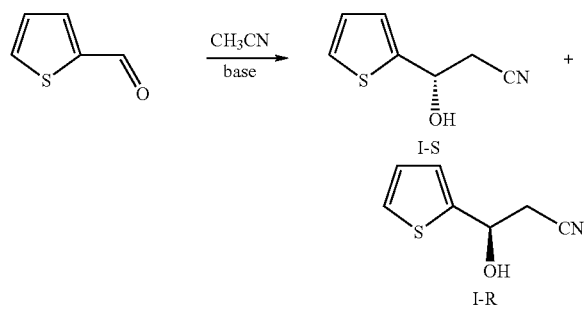

or by nucleophilic ring opening of

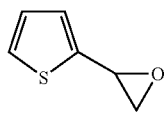

with cyanohydrin analogously to the method described in U.S. Pat. No. 5,136,078.

The bases used for the condensation of thiophene-2-carbaldehyde with acetonitrile are preferably alkali metal and alkaline earth metal hydroxides, such as sodium hydroxide or potassium hydroxide, alkali metal hydrides, such as sodium hydride, alkali metal alkoxides, such as sodium methoxide, sodium ethoxide, sodium tert-butoxide and potassium tert-butoxide and amines, such as dimethylamine, triethylamine, diethylamine, triethylamine or diisopropylamine. Potassium tert-butoxide or sodium tert-butoxide is particularly preferably used.

The solvents used are preferably polar aprotic solvents, such as tetrahydrofuran (THF), dioxane, dimethylformamide or dimethyl sulfoxide, THF being particularly preferred. When using alkali metal hydroxides as bases, however, it is also possible to work under phase transfer conditions, in this case the organic solvents used preferably being aliphatic acyclic ethers, such as diethyl ether, diisopropyl ether, dipropyl ether or methyl tert-butyl ether, the alkali metal hydroxide being introduced into the aqueous phase.

The reaction of the thiophene-2-carbaldehyde preferably takes place at a reaction temperature from −78° C. to 50° C., particularly preferably from −10° to 30° C. and especially at room temperature. The reaction is preferably carried out such that the base is present in the solvent, cooled to the desired reaction temperature and acetonitrile and thiophene-2-carbaldehyde are added successively. It is also possible first to add thiophene-2-carbaldehyde and then acetonitrile, where, however, the first procedure is preferred. The reaction mixture can be worked up in the customary manner, for example by treatment of the reaction mixture with water, extraction of the aqueous phase with a suitable organic solvent and recovery of the alcohol from the organic extract. Solvents suitable for extraction are, for example, acyclic ethers, preferably having 4 to 8 carbon atoms, such as diethyl ether, dipropyl ether, diisopropyl ether, methyl tert-butyl ether, ethyl tert-butyl ether and dibutyl ether, esters, preferably having 3 to 8 carbon atoms, such as methyl acetate and ethyl acetate, aliphatic hydrocarbons, preferably having 5 to 8 C atoms, such as pentane, cyclopentane, hexane, cyclohexane, heptane, cyclooctane, aromatic hydrocarbons, such as benzene, toluene, the xylenes, aliphatic hydrocarbons, preferably having 1 or 2 carbon atoms, such as dichloromethane, trichloromethane, carbon tetrachloride, dichloroethane or tetrachloro-ethane. Preferably, one of the abovementioned ethers is used, in particular diethyl ether or methyl tert-butyl ether.

By means of the process according to the invention, the aminoalcohol II-S is obtained in high optical purity without expensive reagents and without laborious reaction conditions.

The following examples serve to illustrate the invention, but are not to be understood as restricting.

EXAMPLES

1. Preparation of the Enantiomer Mixture of the Alcohols I-R and I-S.

1.1 Reaction at −50° C.

22.0 g (196.4 mmol) of potassium tert-butoxide were introduced into 150 ml of tetrahydrofuran (THF) in a flask with stirring and external cooling, the mixture was cooled to −50° C. and 8.05 g (196.4 mmol) of acetonitrile were added dropwise in the course of 10 minutes. After stirring at −50° C. for one hour, 20.0 g (178.6 mmol) of thiophene-2-carbaldehyde were added. The mixture was allowed to thaw to room temperature, treated with 100 ml of water, the organic phase was separated and the aqueous phase was extracted with 100 ml of methyl tert-butyl ether (MTBE). The combined organic extracts were dried over sodium sulfate and the solvent was removed by distillation under reduced pressure. 24.8 g (91% or theory) of the enantiomer mixture were obtained as a slightly yellow oil having a purity (GC) of more than 95%.

$^1$H-NMR (400 MHz; CDCl$_3$): 7.25 (m, 1H), 7.02 (m, 1H), 6.92 (m, 1H), 5.10 (t, 1H), 4.10 (br s, 1H), 2.75 (d, 2H).

1.2 Reaction at Room Temperature 260 g (2.71 mmol) of sodium tert-butoxide were introduced into 2 l of tetrahydrofuran (THF) in a flask with stirring and an internal thermometer and 110 g (2.71 mol) of acetonitrile were added dropwise in the course of 30 minutes. Care was taken here that the internal temperature did not exceed 35° C. After addition was complete, the mixture was subsequently stirred at room temperature for 30 minutes. 280 g (2.5 mol) of thiophene-2-carbaldehyde were then added in the course of one hour. The mixture was subsequently stirred at room temperature for 2.5 hours, then treated with 1.5 l of water and 1.5 l of methyl tert-butyl ether (MTBE), the organic phase was separated and the aqueous phase was extracted with 100 ml of MTBE. The combined organic extracts were dried over sodium sulfate and the solvent was removed by distillation under reduced pressure. 389 g (100% of theory) of the crude enantiomer mixture were obtained as a pale brown oil having a purity (GC) of more than 97%.

2. Obtainment of I-S 2.1 Obtainment of I-S by Reaction in MTBE

The lipase-containing enzyme preparation from *Pseudomonas* spec. DSM 8246 was prepared analogously to example 1.1 described in EP-A 1 069 183, the enzyme preparation being obtained by spray drying the fermentation supernatant.

5.00 g (32 mmol) of the enantiomer mixture from example 2 were introduced into 20 ml of methyl tert-butyl ether (MTBE) and treated with 19 mmol of the acylating agent and with 0.1 g of lipase-containing enzyme preparation from *Pseudomonas* spec. DSM 8246. The mixture was shaken at room temperature for 6 hours. The enzyme was then filtered off, the filtrate was concentrated and the residue was flash-chromatographed (silica gel 60; hexane/ethyl acetate 1:1). 2.40 g (48% of theory) of the alcohol I-S were obtained. The acylating agents and the enantiomeric excesses thus obtained are listed in the following table. The enantiomeric excess was determined by gas chromatography by means of a chiral column (column: GTA from Chiraldex, 20 m×0.25 mm; split operation; carrier: 70 kpa helium).

| Acylating agent | ee value [%] |
| --- | --- |
| Vinyl hexanoate | 99.4 |
| Succinic anhydride | 99.5 |
| Vinyl propionate | 99.6 |

The enantiomeric excess of the acylated alcohol I-R was in each case 98%.

2.2 Obtainment of I-S by Solvent-Free Reaction

The experimental procedure corresponded to that of example 2.1, where, however, no methyl tert-butyl ether was used. The acylating agent used was 19 mmol of vinyl hexanoate. The separation of the enzyme was carried out by filtration. The alcohol I-S was obtained in a yield of 2.40 g (48% of theory) with an enantiomeric excess of 99.6%.

2.2 Obtainment of I-S in the Presence of Other Enzymes and/or Other Solvents

The experimental procedure corresponded to that of example 2.1, where, however, the enzyme and/or the solvent varied. The acylating agent employed was succinic anhydride. The following table shows the achieved ee values of the alcohol I-S obtained after 50% conversion.

| Lipase | Solvent | ee value [%] |
| --- | --- | --- |
| *Pseudomonas* spec.[1] | Isooctane | 92 |
| Amano PS-C I[2] | MTBE[4] | 88 |
| Amano PS-C II[2] | MTBE[4] | 92 |
| Amano PS-D[3] | MTBE[4] | 91 |

[1]*Pseudomonas* spec. DSM 8246
[2]Product description of Amano Pharmaceutical Co., Tokyo, Japan: enzyme from *Burkholderia cepacia*; immobilized on ceramic
[3]Product description of Amano Pharmaceutical Co., Tokyo, Japan: enzyme from *Burkholderia cepacia*; immobilized on diatomite
[4]Methyl tert-butyl ether 3. Preparation of the Aminoalcohol II-S 3.1 Use of Palladium on Carbon as a Catalyst 2.40 g (15.7 mmol) of the alcohol I-S having an ee value of 99.4% were introduced into a laboratory autoclave in 10 ml of methanol, the solution was treated with 10 mol equivalents of aqueous methylamine (40% strength in water) and with 25 mg of 5% palladium on carbon (from Degussa) and the reaction mixture was hydrogenated at 60° C. and a hydrogen pressure of 100 bar for 24 hours. The catalyst was then filtered off, the solvent was evaporated in vacuo and the residue was recrystallized from cyclohexane/isopropanol. 1.98 g (74% of theory) of the aminoalcohol II-S were obtained as a colorless solid.

Specific rotation: $[\alpha]_D = -12.14°$ at 28° C.
Enantiomeric excess (determination see 2.1): >99.5%
$^1$H-NMR (400 MHz; CDCl$_3$): 7.2 (d, 1H), 6.9 (m, 1H), 5.1 (dd, 1H), 4.1 (br s, 1H), 2.7 (d, 2H); 2.4 (s, 3H); 1.9 (m, 2H).

3.2 Use of Raney Nickel as a Catalyst 28.8 g (0.19 mol) of the alcohol I-S having an ee value of 99.4% were introduced into a laboratory autoclave in 120 ml of methanol, the solution was treated with 12 mol equivalents of aqueous methyl-amine (40% of strength in water) and with 0.6 g of washed Raney nickel (Raney nickel W-02 from Degussa) and the reaction mixture was hydrogenated at 65° C. and a hydrogen pressure of 50 bar for 24 hours. The catalyst was then filtered off, the solvent was evaporated in vacuo and the residue was recrystallized from cyclohexane/isopropanol (10:1). 25.36 g (79% of theory) of the amino-alcohol II-S were obtained as a colorless solid.

Specific rotation: $[\alpha]_D = -12.54°$ at 25° C.
Enantiomeric excess (determination see 2.1): >99.5%
Melting point: 69° C.

I claim:

1. A process for the preparation of enantiomerically pure (S)-3-methylamino-1-(thien-2-yl)propan-1-ol of the formula II-S

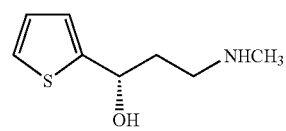

comprising:
a) reacting an enantiomer mixture of the alcohols (S)-3-hydroxy-3-thien-2-ylpropio-nitrile and (R)-3-hydroxy-3-thien-2-ylpropio-nitrile of the formulae I-S and I-R

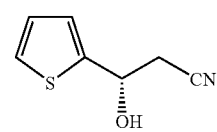

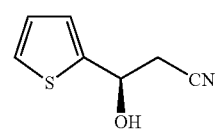

with an acylating agent in the presence of a hydrolase, obtaining a mixture of essentially unacylated alcohol of the formula I-S and essentially acylated alcohol of the formula I-R;
b) separating the alcohol of the formula I-S from the mixture obtained in step a); and
c) reacting the alcohol of the formula I-S with hydrogen and methylamine in the presence of a catalyst to give (S)-3-methylamino-1-(thien-2-yl)propan-1-ol of the formula II-S.

2. The process as claimed in claim 1, where the hydrolase in step a) is selected from among lipases from bacteria of the genera *Burkholderia* or *Pseudomonas*.

3. The process as claimed in claim 2, where the lipase is a lipase from *Burkholderia plantarii*, *Burkholderia cepacia*, *Burkholderia glumae*, *Pseudomonas aeruginosa*, *Pseudomonas fluorescens*, *Pseudomonas fragi*, *Pseudomonas luteola*,

*Pseudomonas vulgaris, Pseudomonas wisconsinensis,* or and *Pseudomonas* spec. DSM 8246.

4. The process as claimed in one of the preceding claim 1, wherein the acylating agent is selected from vinyl, propenyl or isopropenyl esters of aliphatic monocarboxylic acids having 3 to 12 carbon atoms, vinyl, propenyl or isopropenyl esters of aliphatic dicarboxylic acids having 3 to 12 carbon atoms, acid anhydrides of aliphatic monocarboxylic acids having 2 to 12 carbon atoms, or acid anhydrides of aliphatic dicarboxylic acids having 4 to 12 carbon atoms.

5. The process as claimed in claim 1, wherein the reaction in step a) is carried out in a nonaqueous reaction medium.

6. The process as claimed in claim 1, wherein the reaction in step a) is carried out in substance.

7. The process as claimed in claim 1, wherein 1 to 1.5 mol equivalents of the acylating agent, based on the content of alcohol of the formula I-R in the enantiomer mixture, is employed in step a).

8. The process as claimed in claim 1, wherein the enantiomer mixture employed in step a) is the racemate of the alcohols of the formulae I-S and I-R.

9. The process as claimed in claim 1, in wherein the enantiomer mixture of the alcohols of the formulae I-R and I-S employed in step a) is obtained by reaction of thiophene-2-carbaldehyde with acetonitrile in the presence of a base.

* * * * *

UNITED STATES PATENT AND TRADEMARK OFFICE
CERTIFICATE OF CORRECTION

| | |
|---|---|
| PATENT NO. | : 7,435,563 B2 |
| APPLICATION NO. | : 10/522888 |
| DATED | : October 14, 2008 |
| INVENTOR(S) | : Rainer Stürmer |

It is certified that error appears in the above-identified patent and that said Letters Patent is hereby corrected as shown below:

In the Claims:

In Claim 3, in column 15, on line 1, "*Pseudomonas vulgaris, Pseudomonas wisconsinensis*, or and" should read -- *Pseudomonas vulgaris, Pseudomonas wisconsinensis*, or --.

In Claim 4, in column 15, on line 3, "4. The process as claimed in one of the preceding claim 1," should read -- 4. The process as claimed in claim 1, --.

In Claim 9, in column 16, on line 8, "9. The process as claimed in claim 1, in wherein the enan-" should read -- 9. The process as claimed in claim 1, wherein the enan- --.

Signed and Sealed this

Eighth Day of September, 2009

David J. Kappos
*Director of the United States Patent and Trademark Office*